(12) United States Patent
Bali et al.

(10) Patent No.: US 11,523,817 B2
(45) Date of Patent: Dec. 13, 2022

(54) ENDOLUMINAL PURSESTRING DEVICE

(71) Applicant: Covidien LP, Mansfield, MA (US)

(72) Inventors: Sumit Bali, Bengal (IN); Avvln Srinivasa Murthy Aravalli, Hyderabad (IN)

(73) Assignee: COVIDIEN LP, Mansfield, MA (US)

( * ) Notice: Subject to any disclaimer, the term of this patent is extended or adjusted under 35 U.S.C. 154(b) by 298 days.

(21) Appl. No.: 16/857,230

(22) Filed: Apr. 24, 2020

(65) Prior Publication Data

US 2020/0405286 A1    Dec. 31, 2020

Related U.S. Application Data

(60) Provisional application No. 62/867,261, filed on Jun. 27, 2019.

(51) Int. Cl.

| | |
|---|---|
| *A61B 17/04* | (2006.01) |
| *A61B 17/06* | (2006.01) |
| *A61B 17/00* | (2006.01) |
| A61B 34/35 | (2016.01) |
| A61B 17/11 | (2006.01) |

(52) U.S. Cl.
CPC ...... *A61B 17/0469* (2013.01); *A61B 17/0401* (2013.01); *A61B 17/06166* (2013.01); *A61B 34/35* (2016.02); *A61B 2017/00424* (2013.01); *A61B 2017/0409* (2013.01); *A61B 2017/0441* (2013.01); *A61B 2017/1142* (2013.01)

(58) Field of Classification Search
CPC ........ A61B 17/0401; A61B 2017/0409; A61B 2017/1142; A61B 2017/00424
See application file for complete search history.

(56) References Cited

U.S. PATENT DOCUMENTS

| | | |
|---|---|---|
| 3,596,528 A | 8/1971 | Dittrich et al. |
| 3,866,510 A | 2/1975 | Eibes et al. |

(Continued)

FOREIGN PATENT DOCUMENTS

| | | |
|---|---|---|
| EP | 0374088 A1 | 6/1990 |
| EP | 3154446 A1 | 4/2017 |
| JP | 09149906 | 6/1997 |

OTHER PUBLICATIONS

Extended European Search Report corresponding to EP 14 15 8946.5, completed Jun. 20, 2014 and dated Jul. 8, 2014; (9 pp).

(Continued)

*Primary Examiner* — Kelly J Bekker
*Assistant Examiner* — Andrew P. Restaino (57) ABSTRACT

An endoluminal pursestring device is provided and includes a handle assembly, a shaft, an elongated fork, a plurality of surgical fasteners disposed with the shaft, and a suture engaged with the surgical fasteners. The suture is secured to a head of each of the surgical fasteners, and extends proximally through the handle assembly. In use, a distal end of the endoluminal pursestring device is positioned adjacent tissue surrounding a lumen, and the handle assembly is rotated to cause the distal-most surgical fastener to be rotated into the tissue. The following surgical fasteners are also rotated into other portions of the tissue surrounding a lumen. The suture connecting each of the surgical fasteners is then pulled such that the surgical fasteners are pulled together, thereby closing the lumen.

11 Claims, 9 Drawing Sheets

(56) References Cited

U.S. PATENT DOCUMENTS

| | | |
|---|---|---|
| 4,350,491 A | 9/1982 | Steuer |
| 4,730,726 A | 3/1988 | Holzwarth |
| 4,884,572 A | 12/1989 | Bays et al. |
| 5,085,661 A | 2/1992 | Moss |
| 5,144,942 A | 9/1992 | Decarie et al. |
| 5,156,267 A | 10/1992 | Yates, Jr. et al. |
| 5,171,247 A | 12/1992 | Hughett et al. |
| 5,171,249 A | 12/1992 | Stefanchik et al. |
| 5,176,306 A | 1/1993 | Heimerl et al. |
| 5,207,697 A | 5/1993 | Carusillo et al. |
| 5,228,256 A | 7/1993 | Dreveny |
| 5,236,563 A | 8/1993 | Loh |
| 5,246,441 A | 9/1993 | Ross et al. |
| 5,246,450 A | 9/1993 | Thornton et al. |
| 5,312,023 A | 5/1994 | Green et al. |
| 5,330,487 A | 7/1994 | Thornton et al. |
| 5,344,061 A | 9/1994 | Crainich |
| 5,353,929 A | 10/1994 | Foster |
| 5,356,064 A | 10/1994 | Green et al. |
| 5,381,896 A | 1/1995 | Simons |
| 5,382,254 A | 1/1995 | McGarry et al. |
| 5,398,861 A | 3/1995 | Green |
| 5,403,327 A | 4/1995 | Thornton et al. |
| 5,407,070 A | 4/1995 | Bascos et al. |
| 5,433,721 A | 7/1995 | Hooven et al. |
| 5,439,468 A | 8/1995 | Schulze et al. |
| 5,466,243 A | 11/1995 | Schmieding et al. |
| 5,467,911 A | 11/1995 | Tsuruta et al. |
| 5,474,566 A | 12/1995 | Mesi et al. |
| 5,474,567 A | 12/1995 | Stefanchik et al. |
| 5,484,451 A | 1/1996 | Akopov et al. |
| 5,522,844 A | 6/1996 | Johnson |
| 5,527,319 A | 6/1996 | Green et al. |
| 5,553,765 A | 9/1996 | Knodel et al. |
| 5,562,685 A | 10/1996 | Mollenauer et al. |
| 5,564,615 A | 10/1996 | Bishop et al. |
| 5,582,615 A | 12/1996 | Foshee et al. |
| 5,582,616 A | 12/1996 | Bolduc et al. |
| 5,584,425 A | 12/1996 | Savage et al. |
| 5,588,581 A | 12/1996 | Conlon et al. |
| 5,601,571 A | 2/1997 | Moss |
| 5,601,573 A | 2/1997 | Fogelberg et al. |
| 5,607,436 A | 3/1997 | Pratt et al. |
| 5,626,613 A | 5/1997 | Schmieding |
| 5,628,752 A | 5/1997 | Asnis et al. |
| 5,649,931 A | 7/1997 | Bryant et al. |
| 5,662,662 A | 9/1997 | Bishop et al. |
| 5,681,330 A | 10/1997 | Hughett et al. |
| 5,683,401 A | 11/1997 | Schmieding et al. |
| 5,685,474 A | 11/1997 | Seeber |
| 5,697,935 A | 12/1997 | Moran et al. |
| 5,704,534 A | 1/1998 | Huitema et al. |
| 5,709,692 A | 1/1998 | Mollenauer et al. |
| 5,728,116 A | 3/1998 | Rosenman |
| 5,730,744 A | 3/1998 | Justin et al. |
| 5,732,806 A | 3/1998 | Foshee et al. |
| 5,735,854 A | 4/1998 | Caron et al. |
| 5,741,268 A | 4/1998 | Schutz |
| 5,762,255 A | 6/1998 | Chrisman et al. |
| 5,782,844 A | 7/1998 | Yoon et al. |
| 5,792,165 A | 8/1998 | Klieman et al. |
| 5,810,882 A | 9/1998 | Bolduc et al. |
| 5,824,008 A | 10/1998 | Bolduc et al. |
| 5,830,221 A | 11/1998 | Stein et al. |
| 5,843,087 A | 12/1998 | Jensen et al. |
| 5,897,564 A | 4/1999 | Schulze et al. |
| 5,904,693 A | 5/1999 | Dicesare et al. |
| 5,904,696 A | 5/1999 | Rosenman |
| 5,910,105 A | 6/1999 | Swain et al. |
| 5,911,722 A | 6/1999 | Adler et al. |
| 5,928,244 A | 7/1999 | Tovey et al. |
| 5,928,252 A | 7/1999 | Steadman et al. |
| 5,931,844 A | 8/1999 | Thompson et al. |
| 5,941,439 A | 8/1999 | Kammerer et al. |
| 5,954,259 A | 9/1999 | Viola et al. |
| 5,961,524 A | 10/1999 | Crombie |
| 5,964,772 A | 10/1999 | Bolduc et al. |
| 5,976,160 A | 11/1999 | Crainich |
| 5,997,552 A | 12/1999 | Person et al. |
| 6,010,513 A | 1/2000 | Tormala et al. |
| 6,013,991 A | 1/2000 | Philipp |
| 6,039,753 A | 3/2000 | Meislin |
| 6,074,395 A | 6/2000 | Trott et al. |
| 6,099,537 A | 8/2000 | Sugai et al. |
| 6,126,670 A | 10/2000 | Walker et al. |
| 6,132,435 A | 10/2000 | Young |
| 6,146,387 A | 11/2000 | Trott et al. |
| 6,183,479 B1 | 2/2001 | Tormala et al. |
| 6,228,098 B1 | 5/2001 | Kayan et al. |
| 6,235,058 B1 | 5/2001 | Huene |
| 6,241,736 B1 | 6/2001 | Sater et al. |
| 6,261,302 B1 | 7/2001 | Voegele et al. |
| 6,296,656 B1 | 10/2001 | Bolduc et al. |
| 6,330,964 B1 | 12/2001 | Kayan et al. |
| 6,387,113 B1 | 5/2002 | Hawkins et al. |
| 6,402,757 B1 | 6/2002 | Moore, III et al. |
| 6,402,780 B2 | 6/2002 | Williamson, IV et al. |
| 6,425,900 B1 | 7/2002 | Knodel et al. |
| 6,439,446 B1 | 8/2002 | Perry et al. |
| 6,440,136 B1 | 8/2002 | Gambale et al. |
| 6,450,391 B1 | 9/2002 | Kayan et al. |
| 6,457,625 B1 | 10/2002 | Tormala et al. |
| 6,551,333 B2 | 4/2003 | Kuhns et al. |
| 6,562,051 B1 | 5/2003 | Bolduc et al. |
| 6,572,626 B1 | 6/2003 | Knodel et al. |
| 6,589,249 B2 | 7/2003 | Sater et al. |
| 6,592,593 B1 | 7/2003 | Parodi et al. |
| 6,626,916 B1 | 9/2003 | Yeung et al. |
| 6,632,228 B2 | 10/2003 | Fortier et al. |
| 6,652,538 B2 | 11/2003 | Kayan et al. |
| 6,663,656 B2 | 12/2003 | Schmieding et al. |
| 6,666,854 B1 | 12/2003 | Lange |
| 6,695,867 B2 | 2/2004 | Ginn et al. |
| 6,733,506 B1 | 5/2004 | McDevitt et al. |
| 6,743,240 B2 | 6/2004 | Smith et al. |
| 6,749,621 B2 | 6/2004 | Pantages et al. |
| 6,755,836 B1 | 6/2004 | Lewis |
| 6,773,438 B1 | 8/2004 | Knodel et al. |
| 6,800,081 B2 | 10/2004 | Parodi |
| 6,811,552 B2 | 11/2004 | Weil, Sr. et al. |
| 6,824,548 B2 | 11/2004 | Smith et al. |
| 6,837,893 B2 | 1/2005 | Miller |
| 6,840,943 B2 | 1/2005 | Kennefick et al. |
| 6,843,794 B2 | 1/2005 | Sixto, Jr. et al. |
| 6,869,435 B2 | 3/2005 | Blake, III |
| 6,884,248 B2 | 4/2005 | Bolduc et al. |
| 6,887,244 B1 | 5/2005 | Walker et al. |
| 6,893,446 B2 | 5/2005 | Sater et al. |
| 6,905,057 B2 | 6/2005 | Swayze et al. |
| 6,929,661 B2 | 8/2005 | Bolduc et al. |
| 6,942,674 B2 | 9/2005 | Belef et al. |
| 6,945,979 B2 | 9/2005 | Kortenbach et al. |
| 6,960,217 B2 | 11/2005 | Bolduc |
| 6,966,919 B2 | 11/2005 | Sixto, Jr. et al. |
| 6,988,650 B2 | 1/2006 | Schwemberger et al. |
| 7,000,819 B2 | 2/2006 | Swayze et al. |
| 7,070,601 B2 | 7/2006 | Culbert et al. |
| 7,122,028 B2 | 10/2006 | Looper et al. |
| 7,128,754 B2 | 10/2006 | Bolduc |
| 7,147,657 B2 | 12/2006 | Chiang et al. |
| 7,204,847 B1 | 4/2007 | Gambale |
| 7,261,716 B2 | 8/2007 | Strobel et al. |
| 7,357,287 B2 | 4/2008 | Shelton, IV et al. |
| 7,380,696 B2 | 6/2008 | Shelton, IV et al. |
| 7,404,508 B2 | 7/2008 | Smith et al. |
| 7,410,086 B2 | 8/2008 | Ortiz et al. |
| 7,434,717 B2 | 10/2008 | Shelton, IV et al. |
| 7,461,574 B2 | 12/2008 | Lewis et al. |
| 7,491,232 B2 | 2/2009 | Bolduc et al. |
| 7,544,198 B2 | 6/2009 | Parodi |
| 7,591,842 B2 | 9/2009 | Parodi |
| 7,611,521 B2 | 11/2009 | Lubbers et al. |
| 7,637,905 B2 | 12/2009 | Saadat et al. |
| 7,637,932 B2 | 12/2009 | Bolduc et al. |

(56) References Cited

U.S. PATENT DOCUMENTS

| | | | |
|---|---|---|---|
| 7,670,362 | B2 | 3/2010 | Zergiebel |
| 7,740,159 | B2 | 6/2010 | Shelton, IV et al. |
| 7,758,612 | B2 | 7/2010 | Shipp |
| 7,811,312 | B2 | 10/2010 | Stevens et al. |
| 7,819,884 | B2 | 10/2010 | Lee et al. |
| 7,823,267 | B2 | 11/2010 | Bolduc |
| 7,828,838 | B2 | 11/2010 | Bolduc et al. |
| 7,862,573 | B2 | 1/2011 | Darois et al. |
| 7,867,252 | B2 | 1/2011 | Criscuolo et al. |
| 7,905,890 | B2 | 3/2011 | Whitfield et al. |
| 7,913,892 | B2 | 3/2011 | Cole et al. |
| 7,922,061 | B2 | 4/2011 | Shelton, IV et al. |
| 7,922,063 | B2 | 4/2011 | Zemlok et al. |
| 7,931,660 | B2 | 4/2011 | Aranyi et al. |
| 7,959,663 | B2 | 6/2011 | Bolduc |
| 7,959,670 | B2 | 6/2011 | Bolduc |
| 8,002,811 | B2 | 8/2011 | Corradi et al. |
| 8,006,365 | B2 | 8/2011 | Levin et al. |
| 8,034,076 | B2 | 10/2011 | Criscuolo et al. |
| 8,062,306 | B2 | 11/2011 | Nobis et al. |
| 8,075,570 | B2 | 12/2011 | Bolduc et al. |
| 8,083,752 | B2 | 12/2011 | Bolduc |
| 8,087,142 | B2 | 1/2012 | Levin et al. |
| 8,092,519 | B2 | 1/2012 | Bolduc |
| 8,114,099 | B2 | 2/2012 | Shipp |
| 8,114,101 | B2 | 2/2012 | Criscuolo et al. |
| 8,152,820 | B2 | 4/2012 | Mohamed et al. |
| 8,181,840 | B2 | 5/2012 | Milliman |
| 8,216,254 | B2 | 7/2012 | McLean et al. |
| 8,216,272 | B2 | 7/2012 | Shipp |
| 8,231,639 | B2 | 7/2012 | Bolduc et al. |
| 8,282,670 | B2 | 10/2012 | Shipp |
| 8,292,933 | B2 | 10/2012 | Zergiebel |
| 8,323,314 | B2 | 12/2012 | Blier |
| 8,328,823 | B2 | 12/2012 | Aranyi et al. |
| 8,333,776 | B2 | 12/2012 | Cheng et al. |
| 8,343,176 | B2 | 1/2013 | Criscuolo et al. |
| 8,343,184 | B2 | 1/2013 | Blier |
| 8,377,044 | B2 | 2/2013 | Coe et al. |
| 8,382,773 | B2 | 2/2013 | Whitfield et al. |
| 8,382,778 | B2 | 2/2013 | Criscuolo et al. |
| 8,414,627 | B2 | 4/2013 | Corradi et al. |
| 8,424,740 | B2 | 4/2013 | Shelton, IV et al. |
| 8,465,520 | B2 | 6/2013 | Blier |
| 8,474,679 | B2 | 7/2013 | Felix |
| 8,496,684 | B2 * | 7/2013 | Crainich ............ A61B 17/0469 606/232 |
| 8,579,919 | B2 | 11/2013 | Bolduc et al. |
| 8,579,920 | B2 | 11/2013 | Nering et al. |
| 8,597,311 | B2 | 12/2013 | Criscuolo et al. |
| 8,603,135 | B2 | 12/2013 | Mueller |
| 8,672,209 | B2 | 3/2014 | Crainich |
| 8,684,247 | B2 | 4/2014 | Scirica et al. |
| 8,685,044 | B2 | 4/2014 | Bolduc et al. |
| 8,690,889 | B2 | 4/2014 | Colesanti et al. |
| 8,690,897 | B2 | 4/2014 | Bolduc |
| 8,728,098 | B2 | 5/2014 | Daniel et al. |
| 8,728,099 | B2 | 5/2014 | Cohn et al. |
| 8,728,102 | B2 | 5/2014 | Criscuolo et al. |
| 8,728,120 | B2 | 5/2014 | Blier |
| 8,777,969 | B2 | 7/2014 | Kayan |
| 8,821,514 | B2 | 9/2014 | Aranyi |
| 8,821,522 | B2 | 9/2014 | Criscuolo et al. |
| 8,821,557 | B2 | 9/2014 | Corradi et al. |
| 8,852,215 | B2 | 10/2014 | Criscuolo et al. |
| 8,894,669 | B2 | 11/2014 | Nering et al. |
| 8,920,439 | B2 | 12/2014 | Cardinale et al. |
| 8,926,637 | B2 | 1/2015 | Zergiebel |
| 9,017,345 | B2 | 4/2015 | Taylor et al. |
| 9,023,065 | B2 | 5/2015 | Bolduc et al. |
| 9,028,495 | B2 | 5/2015 | Mueller et al. |
| 9,186,138 | B2 | 11/2015 | Corradi et al. |
| 9,259,221 | B2 | 2/2016 | Zergiebel |
| 9,282,961 | B2 | 3/2016 | Whitman et al. |
| 9,332,983 | B2 | 5/2016 | Shipp |
| 9,345,462 | B2 | 5/2016 | Weitzner et al. |
| 9,351,728 | B2 | 5/2016 | Sniffin et al. |
| 9,351,733 | B2 | 5/2016 | Fischvogt |
| 9,358,004 | B2 | 6/2016 | Sniffin et al. |
| 9,358,010 | B2 | 6/2016 | Wenchell et al. |
| 9,364,231 | B2 | 6/2016 | Wenchell |
| 9,364,274 | B2 | 6/2016 | Zergiebel |
| 9,386,983 | B2 | 7/2016 | Swensgard et al. |
| 9,402,623 | B2 | 8/2016 | Kayan |
| 9,445,814 | B2 | 9/2016 | Ranucci et al. |
| 9,486,218 | B2 | 11/2016 | Criscuolo et al. |
| 9,526,498 | B2 | 12/2016 | Reed |
| 9,615,830 | B2 | 4/2017 | Ranucci et al. |
| 9,655,621 | B2 | 5/2017 | Abuzaina et al. |
| 9,662,106 | B2 | 5/2017 | Corradi et al. |
| 9,668,730 | B2 | 6/2017 | Sniffin et al. |
| 9,783,329 | B2 | 10/2017 | Sniffin et al. |
| 9,788,833 | B2 | 10/2017 | Zergiebel et al. |
| 9,801,633 | B2 | 10/2017 | Sholev et al. |
| 9,867,620 | B2 | 1/2018 | Fischvogt et al. |
| 9,987,010 | B2 | 6/2018 | Zergiebel |
| 10,070,860 | B2 | 9/2018 | Zergiebel |
| 10,299,780 | B2 * | 5/2019 | Catanese, III ...... A61B 17/0487 |
| 2003/0009441 | A1 | 1/2003 | Holsten et al. |
| 2003/0074023 | A1 | 4/2003 | Kaplan et al. |
| 2003/0114839 | A1 | 6/2003 | Looper et al. |
| 2004/0030354 | A1 | 2/2004 | Leung et al. |
| 2004/0092937 | A1 | 5/2004 | Criscuolo et al. |
| 2005/0177180 | A1 * | 8/2005 | Kaganov ............ A61B 17/0057 606/151 |
| 2005/0222665 | A1 | 10/2005 | Aranyi |
| 2006/0129152 | A1 | 6/2006 | Shipp |
| 2006/0129154 | A1 | 6/2006 | Shipp |
| 2007/0038220 | A1 | 2/2007 | Shipp |
| 2007/0088390 | A1 | 4/2007 | Paz et al. |
| 2007/0106317 | A1 | 5/2007 | Shelton et al. |
| 2007/0162030 | A1 | 7/2007 | Aranyi et al. |
| 2008/0086154 | A1 | 4/2008 | Taylor et al. |
| 2008/0097523 | A1 | 4/2008 | Bolduc et al. |
| 2008/0312687 | A1 | 12/2008 | Blier |
| 2009/0048613 | A1 | 2/2009 | Surti |
| 2009/0112234 | A1 | 4/2009 | Crainich et al. |
| 2009/0118776 | A1 | 5/2009 | Kelsch et al. |
| 2009/0188965 | A1 | 7/2009 | Levin et al. |
| 2009/0210006 | A1 | 8/2009 | Cohen et al. |
| 2010/0270354 | A1 | 10/2010 | Rimer et al. |
| 2011/0022065 | A1 | 1/2011 | Shipp |
| 2011/0288583 | A1 | 11/2011 | Goraltchouk et al. |
| 2011/0295282 | A1 | 12/2011 | Glick et al. |
| 2012/0022557 | A1 * | 1/2012 | Cabiri ................ A61B 17/064 606/139 |
| 2012/0059397 | A1 | 3/2012 | Criscuolo et al. |
| 2012/0059417 | A1 | 3/2012 | Norton et al. |
| 2012/0109157 | A1 | 5/2012 | Criscuolo et al. |
| 2013/0238021 | A1 | 9/2013 | Gross et al. |
| 2014/0005678 | A1 | 1/2014 | Shelton, IV et al. |
| 2014/0014707 | A1 | 1/2014 | Onukuri et al. |
| 2014/0081324 | A1 | 3/2014 | Sengun |
| 2014/0200587 | A1 | 7/2014 | Pompee et al. |
| 2014/0243855 | A1 | 8/2014 | Sholev et al. |
| 2014/0243893 | A1 | 8/2014 | Santangelo et al. |
| 2015/0032130 | A1 | 1/2015 | Russo |
| 2015/0133970 | A1 | 5/2015 | Ranucci et al. |
| 2015/0327859 | A1 | 11/2015 | Bolduc |
| 2016/0007991 | A1 | 1/2016 | Bolduc |
| 2016/0007996 | A1 | 1/2016 | Bolduc |
| 2016/0074034 | A1 | 3/2016 | Shipp |
| 2016/0166255 | A1 | 6/2016 | Fischvogt |
| 2016/0249912 | A1 | 9/2016 | Fischvogt |
| 2016/0270835 | A1 | 9/2016 | Reed |
| 2016/0278766 | A1 | 9/2016 | Wenchell et al. |
| 2016/0338694 | A1 | 11/2016 | Kayan |
| 2016/0345967 | A1 * | 12/2016 | Sniffin .................. A61B 90/03 |
| 2017/0086825 | A1 | 3/2017 | Henderson et al. |
| 2017/0231631 | A1 | 8/2017 | Abuzaina et al. |
| 2017/0265859 | A1 | 9/2017 | Sniffin et al. |
| 2018/0042591 | A1 | 2/2018 | Russo et al. |

(56) References Cited

U.S. PATENT DOCUMENTS

2018/0116670 A1 5/2018 Fischvogt et al.
2018/0256149 A1 9/2018 Gustafson et al.

OTHER PUBLICATIONS

Extended European Search Report corresponding to EP 14 17 8107.0, completed Nov. 24, 2014 and dated Dec. 3, 2014; (5 pp).
Extended European Search Report corresponding to EP 14 17 4656.0, completed Jan. 16, 2015 and dated Jan. 26, 2015; (7 pp).
Extended European Search Report corresponding to EP 14 18 4907.5, completed Jan. 12, 2015 and dated Jan. 27, 2015; (9 pp).
European Search Report corresponding to EP 14 18 1900.3, completed Mar. 31, 2015 and dated Apr. 9, 2015; 7pp.
Extended European Search Report corresponding to EP 14 19 7885.8 dated Apr. 30, 2015.
Extended European Search Report corresponding to EP No. 11 25 0549.0, completed Sep. 9, 2013 and dated Sep. 17, 2013; 9 pages.
Extended European Search Report corresponding to EP 14 15 9394.7, completed Apr. 16, 2014 and dated Apr. 29, 2014; 8 pages.
European Search Report corresponding to EP 10 01 2659.8, completed Dec. 21, 2010; dated Jan. 3, 2011; 3 pages.
European Search Report corresponding to EP 10 01 2646.5, completed Feb. 11, 2011; dated Feb. 22, 2011.
Extended European Search Report corresponding to EP 14 15 1663.3 dated Jun. 7, 2016.
Supplementary European Search Report corresponding to EP 14 81 7036 dated Feb. 2, 2017.
European Search Report corresponding to EP 17 15 7259.7 dated May 10, 2017.
Chinese First Office Action corresponding to CN 201480037169.2 dated Jun. 29, 2017.
Chinese First Office Action corresponding to CN 201410418879.1 dated Jun. 29, 2017.
European Office Action corresponding to EP 14 17 8107.0 dated Oct. 12, 2017.
Australian Examination Report No. 1 corresponding to AU 2014200870 dated Oct. 26, 2017.
Chinese Second Office Action corresponding to CN 201410090675 dated Nov. 6, 2017.
Japanese Office Action corresponding to JP 2014-048652 dated Nov. 14, 2017.
Japanese Office Action corresponding to JP 2014-047708 dated Nov. 14, 2017.
Chinese Second Office Action corresponding to CN 2014103063407 dated Feb. 1, 2018.
Australian Examination Report No. 1 corresponding to AU 2014202970 dated Mar. 9, 2018.
Japanese Office Action corresponding to JP 2014-048652 dated Mar. 15, 2018.
Chinese Second Office Action corresponding to CN 201480077682.4 dated Mar. 21, 2018.
Australian Examination Report No. 1 corresponding to AU 2014202972 dated Mar. 27, 2018.
European Office Action corresponding to Patent Application EP 14 15 8946.5 dated Apr. 26, 2018.
Japanese Office Action corresponding to Patent Application JP 2014-132105 dated May 1, 2018.
Japanese Office Action corresponding to Patent Application JP 2014-047708 dated May 14, 2018.
Chinese Second Office Action corresponding to Patent Application CN 2014103559671 dated May 25, 2018.
Australian Examination Report No. 1 corresponding to Patent Application AU 2014302551 dated Jul. 16, 2018.
Japanese Office Action corresponding to Patent Application JP 2014-047708 dated Aug. 15, 2018.

\* cited by examiner

ENDOLUMINAL PURSESTRING DEVICE

CROSS-REFERENCE TO RELATED APPLICATIONS

This application claims the benefit of and priority to U.S. Provisional Patent Application No. 62/867,261 filed Jun. 27, 2019, the entire disclosure of which is incorporated by reference herein.

BACKGROUND

1. Technical Field

The disclosure relates to a surgical instrument for performing endoluminal surgical procedures. More specifically, the disclosure relates to an endoluminal pursestring device for endoscopically applying surgical fasteners and creating a pursestring about a lumen.

2. Background of Related Art

Various surgical procedures include the need to at least partially close off a tubular lumen. For instance, it may be desired to seal off a lumen to help prevent cancerous cells from spreading to healthy tissue during surgery.

One method of closing off a lumen prior to surgery is to create a pursestring about the perimeter of the lumen, and pull the pursestring taut to close or substantially close the lumen. To close a lumen during a transanal total mesorectal excision (taTME) surgery, for example, a surgeon may create a manual pursestring through a small opening in an access port. Due to the size restrictions of the access port, the amount the surgeon can move his or her hand is highly restricted, which often makes it difficult for the surgeon to create the desired pursestring.

SUMMARY

The disclosure relates to an endoluminal pursestring device including a handle assembly, a shaft extending distally from the handle assembly and defining a longitudinal axis, an elongated fork extending distally from the handle assembly, a plurality of surgical fasteners disposed at least partially within the shaft, and a suture engaged with at least one of the surgical fasteners. Rotation of the handle assembly about the longitudinal axis relative to the shaft causes distal translation of the plurality of surgical fasteners and of the suture relative to the shaft.

In disclosed embodiments, the elongated fork includes a first tine and a second tine defining a slot therebetween. A head of each of the surgical fasteners is positioned within the slot.

It is further disclosed that the shaft extends distally of a distal-most end of the elongated fork.

Further, the shaft defines an elongated lumen extending therethrough, and an interior wall of the shaft defines a thread. A body portion of each of the surgical fasteners engages the thread of the interior wall of the shaft.

The disclosure also relates to an endoluminal pursestring device including a shaft defining a longitudinal axis and an elongated lumen extending therethrough, a handle assembly extending proximally from the shaft and defining a channel therethrough, and an elongated fork extending distally from the handle assembly and defining a channel extending therethrough. The elongated lumen of the shaft, the channel of the handle assembly, and the channel of the elongated fork are all co-axial with each other.

In disclosed embodiments, the endoluminal pursestring device includes a plurality of surgical fasteners disposed at least partially within the shaft. Further, rotation of the handle assembly about the longitudinal axis relative to the shaft causes distal translation of the plurality of fasteners relative to the shaft.

It is also disclosed that the endoluminal pursestring device includes a suture engaged with at least one surgical fastener of the plurality of surgical fasteners. The suture extends through the channel of the elongated fork, through the channel of the handle assembly, and through a proximal opening of the channel of the handle assembly.

In embodiments, an interior wall of the shaft defines a thread and a body portion of each surgical fastener engages the thread.

Additionally, each surgical fastener includes a head that is positioned within a slot defined between a first tine and second tine of the elongated fork.

The disclosure also relates to an endoluminal pursestring device including a handle assembly, a shaft extending distally from the handle assembly and defining a longitudinal axis, a plurality of surgical fasteners disposed within the shaft, and a suture engaged with each surgical fastener within the shaft.

In embodiments, the suture extends completely through a channel extending longitudinally through the handle assembly.

It is also disclosed that a distal end of the shaft includes a notch defined by a first portion of the shaft extending distally beyond a second portion of the shaft. Additionally, a distal-most surgical fastener is distally translatable relative to the shaft such that a first portion of the distal-most surgical fastener is within the notch and a second portion of the distal-most surgical fastener is proximal of the notch.

BRIEF DESCRIPTION OF THE DRAWINGS

Embodiments of the disclosure are described herein with reference to the accompanying drawings, wherein.

DETAILED DESCRIPTION OF EMBODIMENTS

Embodiments of the endoluminal pursestring device are described in detail with reference to the drawings, in which like reference numerals designate identical or corresponding elements in each of the several views. As used herein the term "distal" refers to that portion of the endoluminal pursestring device that is farther from the user, while the term "proximal" refers to that portion of the endoluminal pursestring device that is closer to the user.

Referring initially to FIGS. 1-4, a surgical instrument or endoluminal pursestring device is shown and generally indicated as reference character 10. Endoluminal pursestring device 10 includes a shaft 100 defining a longitudinal axis "A-A," an elongated fork 200, and a handle assembly 300. Shaft 100 defines an elongated cavity or lumen 120 extending longitudinally therethrough. Shaft 100 extends distally from handle assembly 300. Elongated fork 200 includes a first tine 210 and a second tine 220, which define a slot 230 therebetween. Elongated fork 200 extends distally from handle assembly 300, and at least a portion of elongated fork 200 extends through elongated cavity 120 of shaft 100. Additionally, shaft 100 is rotatable about longitudinal axis "A-A" relative to handle assembly 300, and elongated fork 200 is rotationally fixed relative to handle assembly 300. Alternatively, it is envisioned that shaft 100 is rotationally fixed relative to handle assembly 300, and that elongated fork 200 is rotatable about longitudinal axis "A-A" relative to handle assembly 300.

Figure 1:
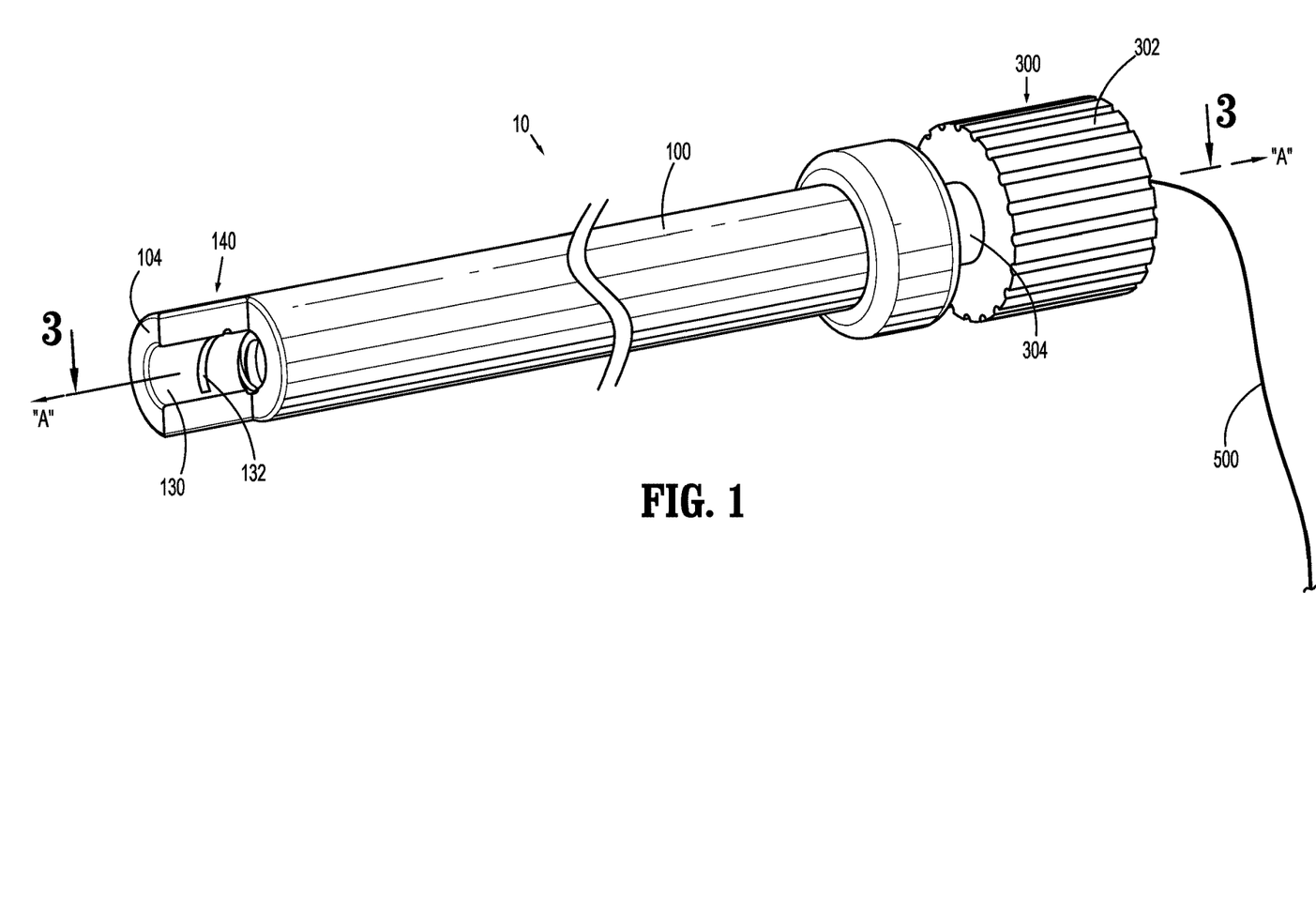
FIG. 1 is a perspective view of an endoluminal pursestring device in accordance with the disclosure.
Figure 2:
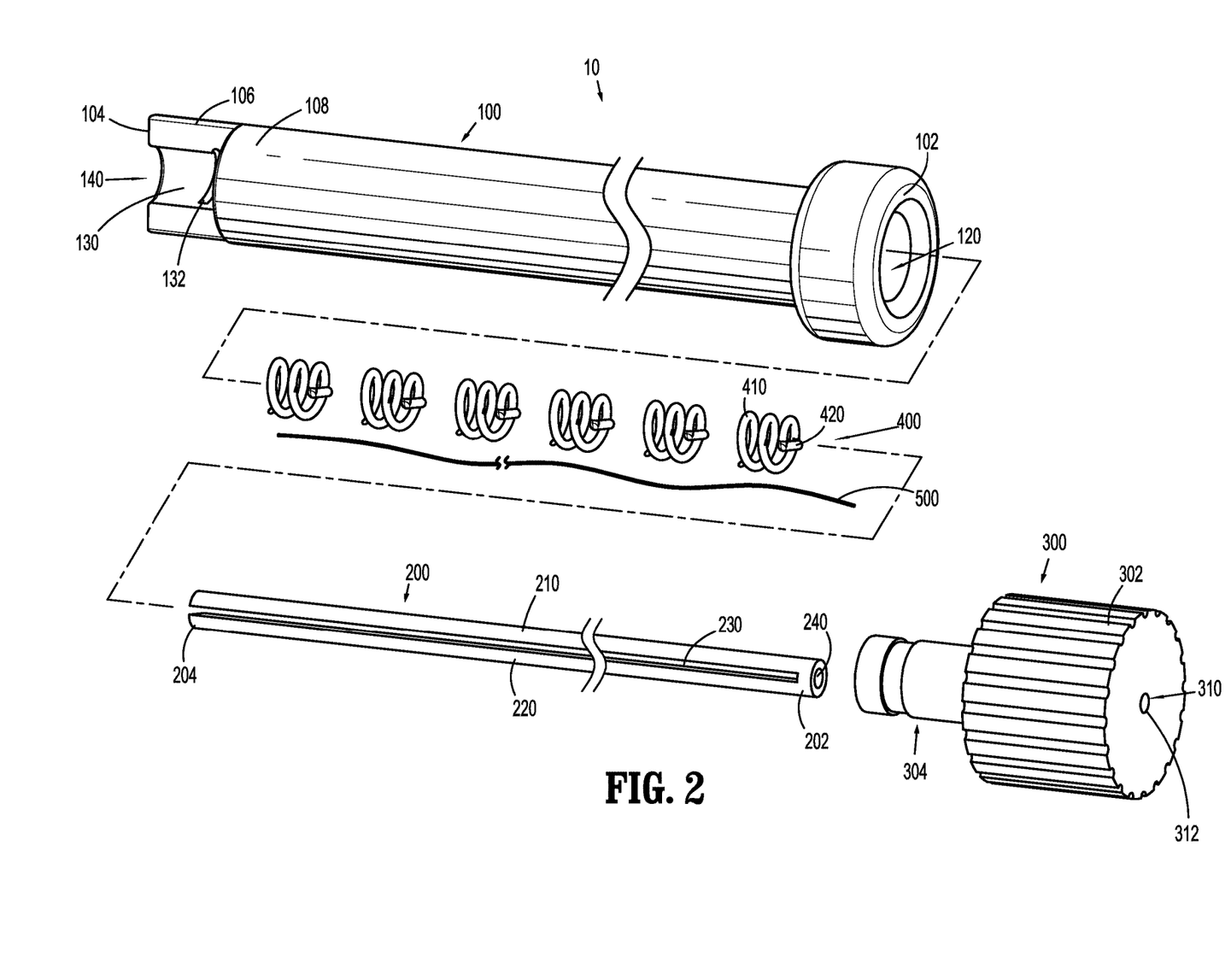
FIG. 2 is a perspective view, with parts separated, of the endoluminal pursestring device of FIG. 1 including a plurality of surgical fasteners and a suture.
Figure 3:
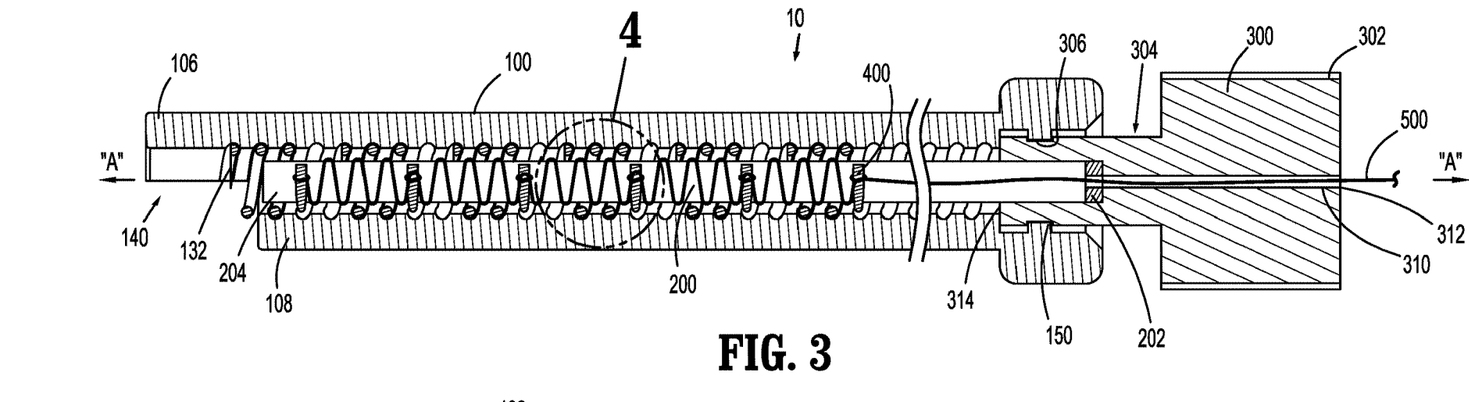
FIG. 3 is a cross-sectional view of the endoluminal pursestring device, as taken through section line 3-3 of FIG. 1.

With continued reference to FIGS. 1-4, elongated cavity 120 of shaft 100 extends between a proximal end 102 of shaft 100 and a distal end 104 of shaft 100, thereby allowing a plurality of surgical fasteners 400 or tacks and a suture 500 to pass therethrough. Additionally, an interior wall 130 of shaft 100 defines a thread 132 in communication with elongated cavity 120. Thread 132 extends along at least a majority of interior wall 130 and is configured to rotationally engage portions of surgical fasteners 400 within elongated cavity 120 of shaft 100. Shaft 100 also includes a notch 140 at its distal end 104. Notch 140 is defined by a first portion 106 of shaft 100 extending beyond a second portion 108 of shaft 100 (FIGS. 2 and 3). As shown in FIGS. 1-3, thread 132 extends beyond a distal-most end of second portion 108 of shaft 100 and into notch 140.

Figure 4:
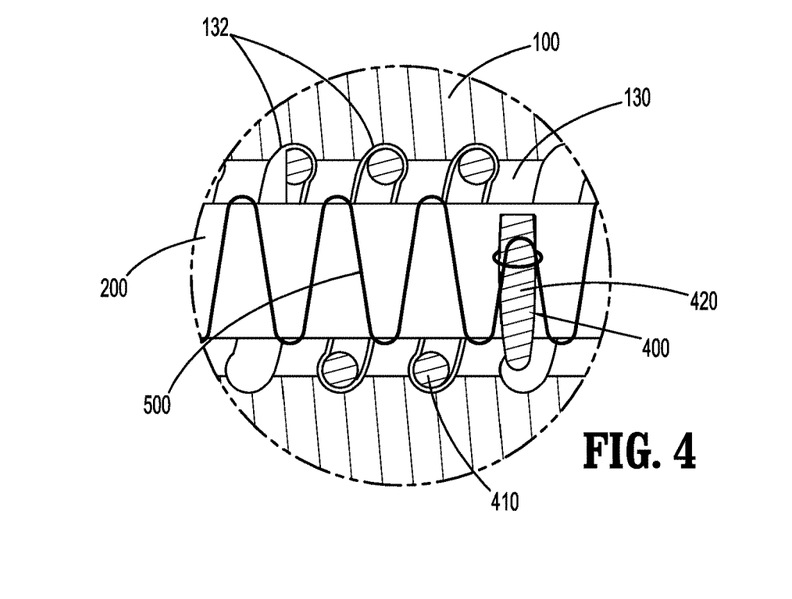
FIG. 4 is an enlarged view of the indicated area of detail of FIG. 3.

Referring now to FIGS. 2-4, elongated fork 200 is positionable at least partially within elongated cavity 120 of shaft 100, and includes a proximal end 202 and a distal end 204. A channel 240 extends from proximal end 202 to distal end 204, and intersects slot 230 along an entirety of the length of slot 230. Channel 240 is configured to allow suture 500 to extend and travel therethrough.

With reference to FIGS. 1-3, handle assembly 300 includes a proximal portion 302, a distal portion 304, and a channel 310. Proximal portion 302 of handle assembly 300 is configured to be gripped by a user, and distal portion 304 of handle assembly 300 is configured to engage shaft 100 and elongated fork 200. Channel 310 extends an entire length of handle assembly 300 and includes a proximal opening 312 and a distal opening 314. Channel 310 is configured to allow suture 500 to extend and travel therethrough.

With specific reference to FIG. 3, a radial ridge 150 on shaft 100 is configured to fit at least partially within a groove 306 of distal portion 304 of handle assembly 300, thereby enabling or facilitating rotational movement between shaft 100 and handle assembly 300. Accordingly, handle assembly 300 is able to rotate about the longitudinal axis "A-A" relative to shaft 100.

With continued reference to FIG. 3, handle assembly 300 is configured to non-rotatably engage elongated fork 200 (e.g., via a snap-fit connection, a friction-fit connection, etc.). More particularly, proximal end 202 of elongated fork 200 is insertable within distal opening 314 of channel 310 of handle assembly 300. For instance, an outer diameter of proximal end 202 of elongated fork 200 may be similar to an inner diameter of distal opening 314 of channel 310 of handle assembly 300, thereby enabling a portion of elongated fork 200 to be frictionally secured within a portion of channel 310 of handle assembly 300. Thus, handle assembly 300 is non-rotatably secured to elongated fork 200, such that rotation of handle assembly 300 about the longitudinal axis "A-A" causes a corresponding rotation of elongated fork 200. Additionally, other mechanical structure (e.g., a set screw, pin, etc.) may be used to non-rotatably secure handle assembly 300 relative to elongated fork 200.

Surgical fasteners 400 include a spiral body portion 410 and a head 420. The body portion 410 of each surgical fastener 400 is positioned circumferentially around or radially outward of elongated fork 200, and head 420 of each surgical fastener 400 is positioned within slot 230 of elongated fork 200, and thus extends laterally between first tine 210 and second tine 220 of elongated fork 200. The spiral body portion 410 of surgical fastener 400 engages thread 132 of shaft 100. Accordingly, rotation of elongated fork 200, and thereby surgical fasteners 400, about the longitudinal axis "A-A" relative to shaft 100, results in surgical fasteners 400 traveling distally relative to shaft 100 while being guided by thread 132 of shaft 100.

While the accompanying figures show six surgical fasteners 400 at least partially within shaft 100, more or fewer surgical fasteners 400 may be included at least partially within shaft 100 (e.g., depending on type of procedure, location of procedure, size of lumen, etc.) without departing from the scope of the disclosure.

Referring to FIGS. 1-4, suture 500 extends through channel 310 of handle assembly 300, through channel 210 of elongated fork 200, and is engaged with each surgical fastener 400 that is disposed at least partially within shaft 100. More particularly, suture 500 is secured (e.g., wrapped around, tied, adhered, etc.) to head 420 of each surgical fastener 400. Further, portions of suture 400 extend radially within spiral body portion 410 of each surgical fastener 400, other than the distal-most surgical fastener 400. That is, one end of suture 500 is secured to head 420 of the distal-most surgical fastener 400, and the other end of suture 500 extends outside (e.g., proximally) of handle assembly 300 where it is able to be gripped by a user (e.g., a surgeon, a robotic hand, etc.). Additionally, a sufficient amount of slack is maintained between adjacent surgical fasteners 400 within shaft 100 to facilitate the placement of surgical fasteners 400 within target tissue.

Figure 5:
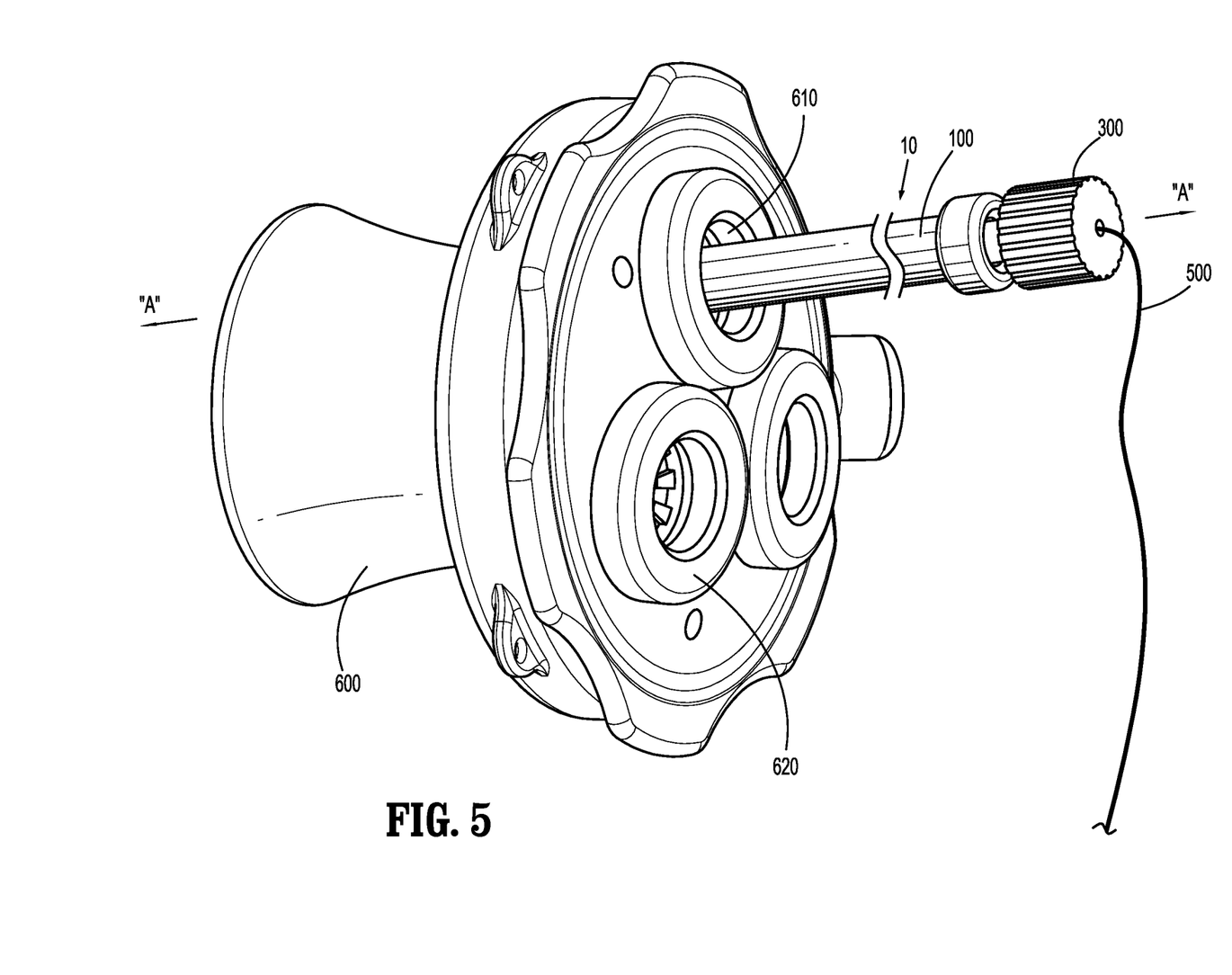
FIG. 5 is a perspective view of the endoluminal pursestring device of FIGS. 1-4 shown partially inserted through an access port.
Figure 6:
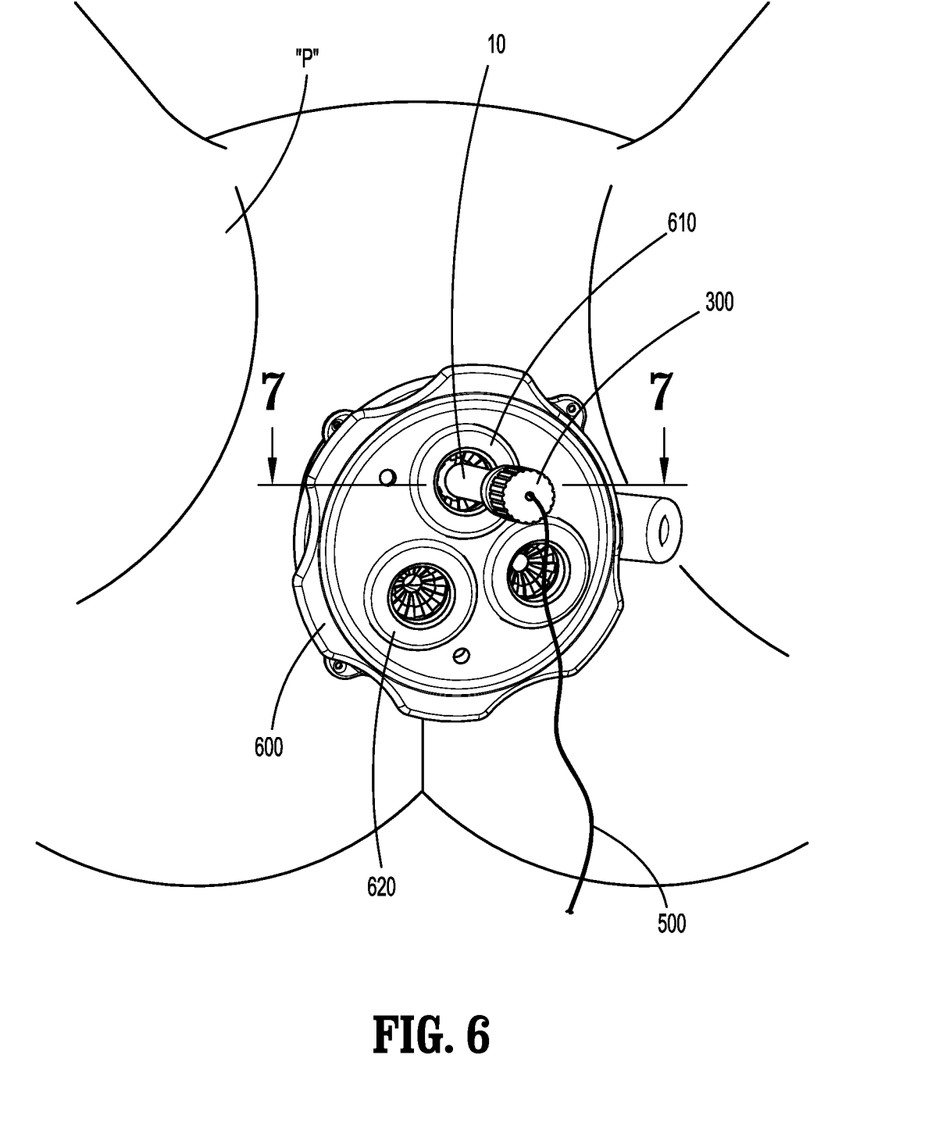
FIG. 6 is a perspective view of the endoluminal pursestring device and access port of FIG. 5 engaged with a patient.
Figure 7:
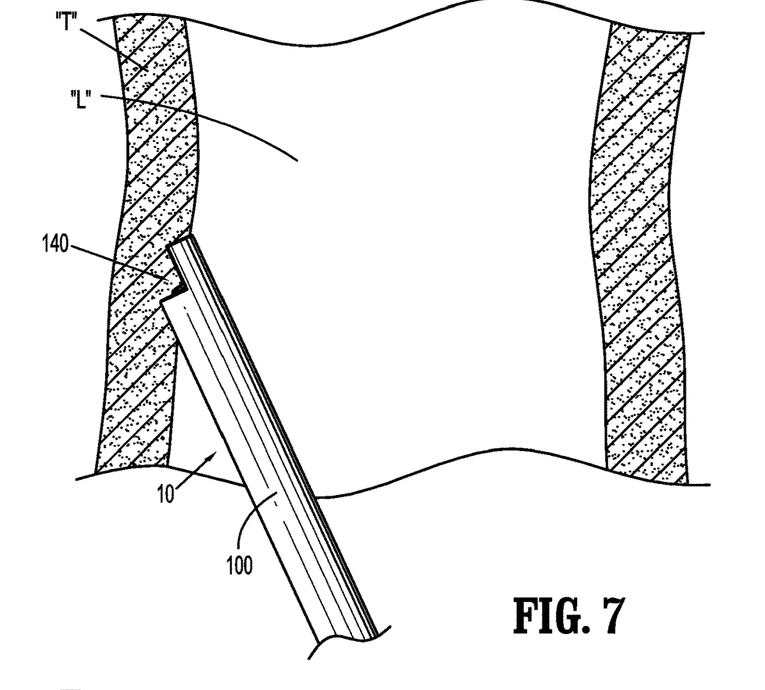
FIG. 7 is a cross-sectional view of the endoluminal pursestring device, as taken through section line 7-7 of FIG. 6, shown with its distal end within a lumen of the patient.

With reference to FIGS. 5-11, use of endoluminal pursestring device 10 is shown. Initially, a port and/or anchor 600 is positioned adjacent or at least partially within a patient "P" (e.g., a naturally-occurring orifice such as the rectum, or a surgically-made opening). Next, a distal end of endoluminal pursestring device 10 is inserted through a first portal 610 of anchor 600 (FIGS. 5 and 6). The distal end of endoluminal pursestring device 10 is advanced within a lumen "L" of the patient "P" until it contacts target tissue "T" (e.g., a wall of lumen "L") (FIG. 7). In this position, target tissue "T" is captured at least partially within notch 140 of shaft 100 to help temporarily secure the distal end of endoluminal pursestring device 10 against the target tissue. Further, an additional tool, such as a surgical grasper, may be inserted through another portal (e.g., second portal 620 of anchor 600) to help move or hold the target tissue "T" to facilitate the temporary securement of the distal end of endoluminal pursestring device 10 with respect to the target tissue "T."

Figure 8:
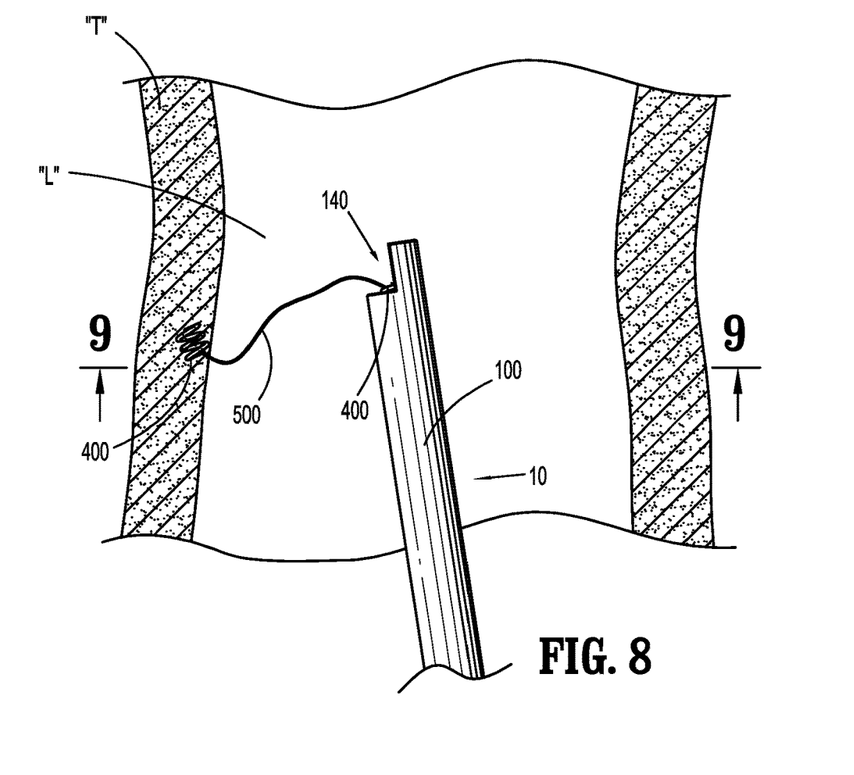
FIG. 8 is a cross-sectional view of the endoluminal pursestring device and lumen of FIG. 7, shown after applying a surgical fastener to a wall of the lumen.

Next, handle assembly 300 is rotated in a first direction (e.g., clockwise) relative to shaft 100 and relative to anchor 600, and about longitudinal axis "A-A." The rotation of handle assembly 300 causes corresponding rotation of elongated fork 200 and surgical fasteners 400 within shaft 100. As surgical fasteners 400 are rotated relative to shaft 100, the spiral body portion 410 of each surgical fastener 400 travels through thread 132 of shaft 100 (see FIGS. 3 and 4). Accordingly, rotation of elongated fork 200 about the longitudinal axis "A-A" relative to shaft 100, results in surgical fasteners 400 traveling distally within elongated cavity 120 of shaft 100 while being guided by thread 132 of shaft 100. The distal and rotational movement of the distal-most fastener 400 causes the distal-most fastener 400 to twist into the target tissue "T." After an appropriate amount of rotation of handle assembly 300 relative to shaft 100, and as shown in FIG. 8, the distal-most surgical fastener 400 is sufficiently secured to or imbedded into the target tissue "T," while suture 500 extends between the distal-most surgical fastener 400 (which is secured to the target tissue "T") and another surgical fastener 400 within shaft 100.

Figure 9:
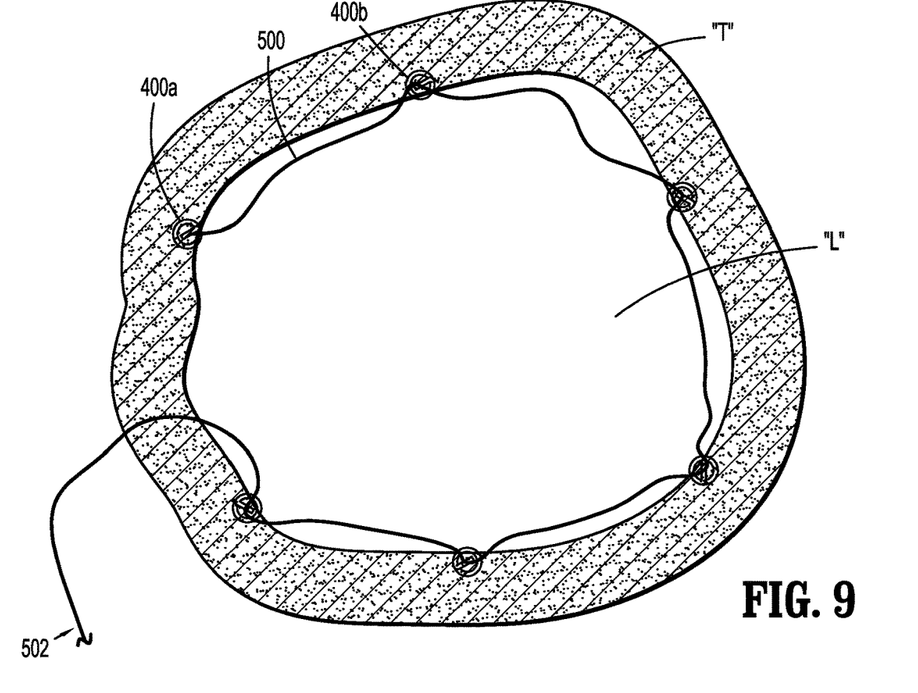
FIG. 9 is a schematic, cross-sectional view of the lumen as taken through section line 9-9 of FIG. 8, showing several surgical fasteners within the wall of the lumen, and a suture extending between the surgical fasteners.
Figure 10:
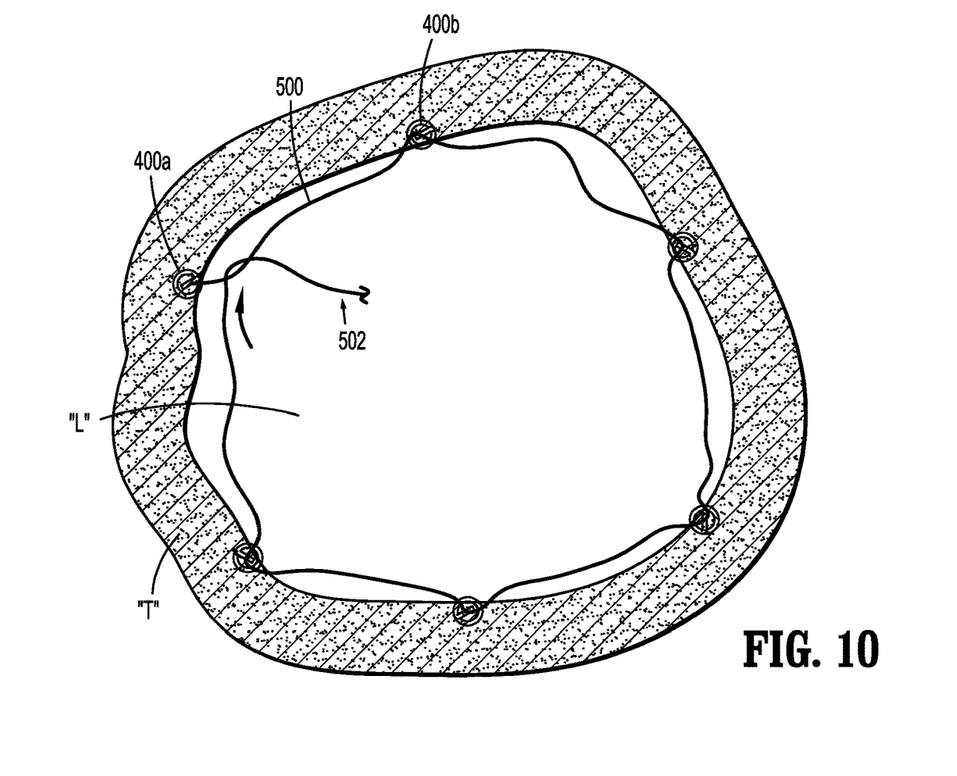
FIG. 10 is a schematic, cross-sectional view of the lumen of FIGS. 7-9, showing several surgical fasteners within the wall of the lumen, and a suture extending between the surgical fasteners, where a portion of the suture is wrapped around another portion of the suture.

The other surgical fasteners 400 within shaft 100 are then individually secured to or imbedded into the target tissue "T" around the perimeter of the lumen "L," while the proximal end or free end 502 of suture 500 remains free or unattached, as shown in FIG. 9. Here, endoluminal pursestring device 10 may be removed from anchor 600. Next, another instrument, such as a surgical grasper (e.g., the same surgical grasper used to facilitate the temporary securement of the distal end of endoluminal pursestring device 10 with respect to the target tissue "T") is used to wrap the free end 502 of suture 500 around the portion of the suture 500 between the first two surgical fasteners applied to the target tissue "T" (indicated as reference characters 400a and 400b in FIGS. 9 and 10).

Figure 11:
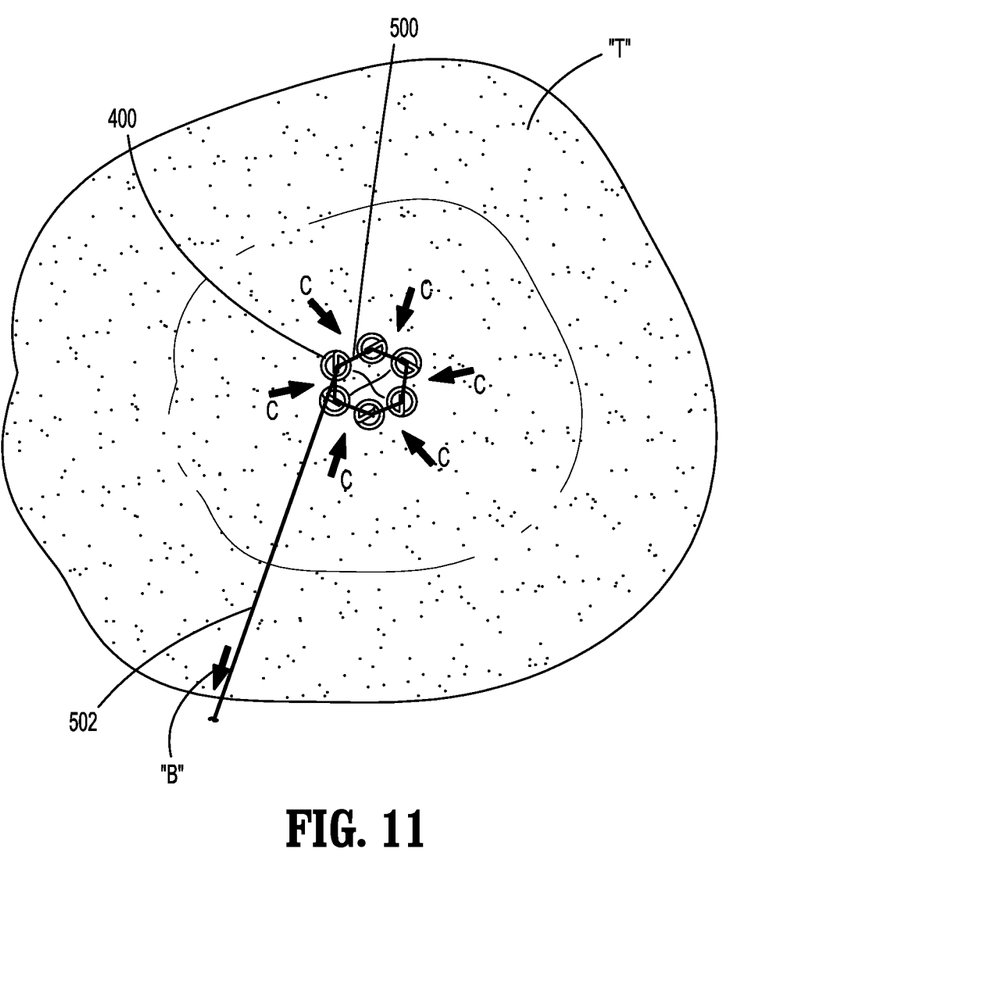
FIG. 11 is a schematic, top view of the lumen of FIGS. 7-10 after the pursestring has been pulled to close the lumen.

Referring now to FIG. 11, the free end 502 of suture 500 is then pulled in the general direction of arrow "B" (e.g., proximally or toward anchor 600) using a surgical grasper, for instance. Since suture 500 is secured to each surgical fastener 400, the force exerted on the free end 502 of suture 500 causes each surgical fastener 400 to move inwardly toward the center of the lumen "L," as indicated by arrows "C" in FIG. 11, thereby closing or substantially closing or occluding the lumen "L."

Surgical instruments such as the endoluminal pursestring device 10 described herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 12:
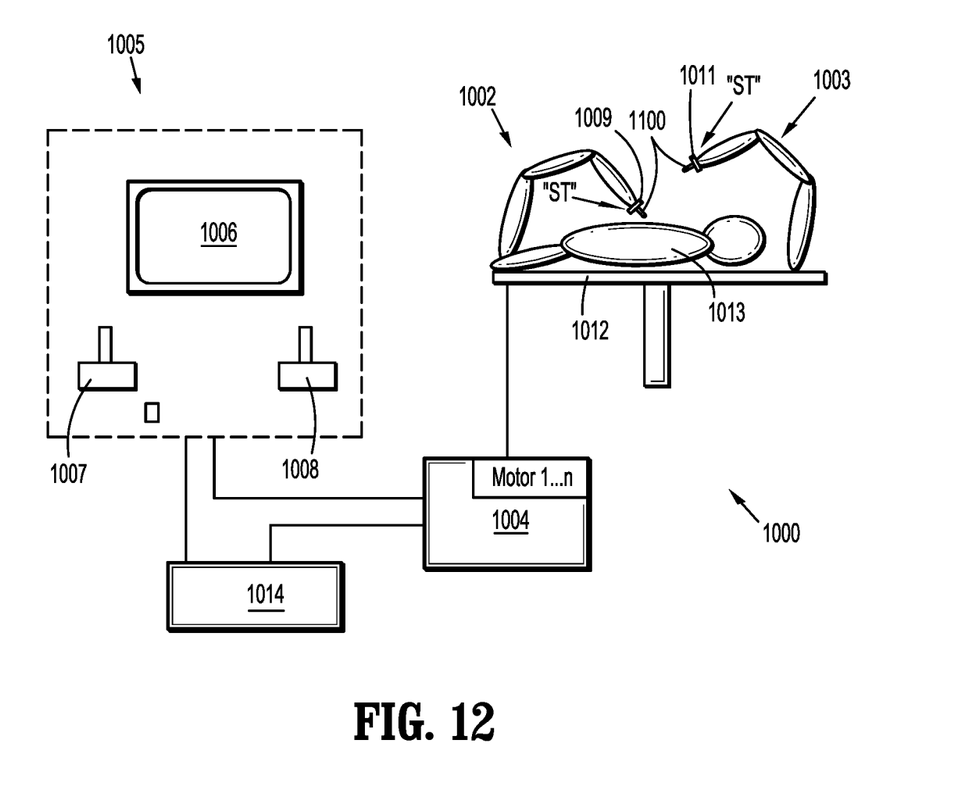
FIG. 12 is a schematic illustration of a surgical system in accordance with the disclosure.

Referring to FIG. 12, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

It should be understood that the foregoing description is only illustrative of the disclosure. Various alternatives and modifications can be devised by those skilled in the art without departing from the disclosure. Accordingly, the disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. An endoluminal pursestring device, comprising:
   a handle assembly;
   a shaft extending distally from the handle assembly and defining a longitudinal axis;
   an elongated fork extending distally from the handle assembly;
   a plurality of surgical fasteners disposed at least partially within the shaft; and
   a suture engaged with at least one surgical fastener of the plurality of surgical fasteners;
   wherein rotation of the handle assembly about the longitudinal axis relative to the shaft causes distal translation of the plurality of surgical fasteners and of the suture relative to the shaft.

2. The endoluminal pursestring device according to claim 1, wherein the elongated fork includes a first tine and a second tine.

3. The endoluminal pursestring device according to claim 2, wherein the elongated fork defines a slot between the first tine and the second tine.

4. The endoluminal pursestring device according to claim 3, wherein each surgical fastener of the plurality of surgical fasteners includes a head, and wherein the head of each surgical fastener of the plurality of surgical fasteners is positioned within the slot of the elongated fork.

5. The endoluminal pursestring device according to claim 1, wherein the shaft extends distally of a distal-most end of the elongated fork.

6. The endoluminal pursestring device according to claim 1, wherein the shaft defines an elongated lumen extending through the shaft, and wherein an interior wall of the shaft defines a thread.

7. The endoluminal pursestring device according to claim 6, wherein a body portion of each surgical fastener of the plurality of surgical fasteners engages the thread of the interior wall of the shaft.

8. An endoluminal pursestring device, comprising:
   a shaft extending along a longitudinal axis and defining an elongated lumen extending longitudinally through the shaft;
   a handle assembly extending proximally from the shaft and defining a channel extending longitudinally through the handle assembly;
   an elongated fork extending distally from the handle assembly and defining a channel extending longitudinally the elongated fork, wherein the elongated lumen of the shaft, the channel of the handle assembly, and the channel of the elongated fork are all co-axial with each other;
   a plurality of surgical fasteners disposed at least partially within the shaft; and
   a suture engaged with at least one surgical fastener of the plurality of surgical fasteners, wherein the suture extends through the channel of the elongated fork, through the channel of the handle assembly, and through a proximal opening of the channel of the handle assembly.

9. The endoluminal pursestring device according to claim 8, wherein rotation of the handle assembly about the longitudinal axis relative to the shaft causes distal translation of the plurality of fasteners relative to the shaft.

10. The endoluminal pursestring device according to claim 8, wherein an interior wall of the shaft defines a thread, and wherein a body portion of each surgical fastener of the plurality of surgical fasteners engages the thread of the interior wall of the shaft.

11. The endoluminal pursestring device according to claim 8, wherein each surgical fastener of the plurality of surgical fasteners includes a head, and wherein the head of each surgical fastener of the plurality of surgical fasteners is positioned within a slot defined between a first tine and second tine of the elongated fork.

* * * * *